(12) United States Patent
Rahman et al.

(10) Patent No.: US 8,148,556 B2
(45) Date of Patent: Apr. 3, 2012

(54) **METHOD OF PRODUCING TIBOLONE METABOLITES BY FERMENTATION WITH *RHIZOPUS STOLONIFER***

(76) Inventors: Attaur Rahman, Islamabad (PK); Muhammed Iqbal Choudhary, Karachi (PK); Syed Adnan Ali Shah, Selangor (MY); Shamsun Nahar Khan, Karachi (PK)

(*) Notice: Subject to any disclaimer, the term of this patent is extended or adjusted under 35 U.S.C. 154(b) by 0 days.

(21) Appl. No.: 13/015,551

(22) Filed: Jan. 27, 2011

(65) Prior Publication Data

US 2011/0124041 A1    May 26, 2011

Related U.S. Application Data

(62) Division of application No. 11/944,475, filed on Nov. 23, 2007, now abandoned.

(51) Int. Cl.
*C07J 1/00*     (2006.01)
*C12P 33/00*    (2006.01)
*C12P 33/06*    (2006.01)

(52) U.S. Cl. .......... 552/612; 552/615; 552/645; 435/52; 435/58

(58) Field of Classification Search .................. 552/612, 552/615, 645
See application file for complete search history.

*Primary Examiner* — Barbara P Badio
(74) *Attorney, Agent, or Firm* — Sarfaraz Niazi

(57) ABSTRACT

A new method of producing metabolites of tibolone comprising fermenting tibolone with *Rhizopus stolonifer* (ATCC 12938) resulting in the formation of $\Delta^4$-Tibolone ($C_{21}H_{28}O_2$), 6β-Hydroxytibolone, and 15β-Hydroxytibolone ($C_{21}H_{28}O_3$) is reported.

1 Claim, 1 Drawing Sheet

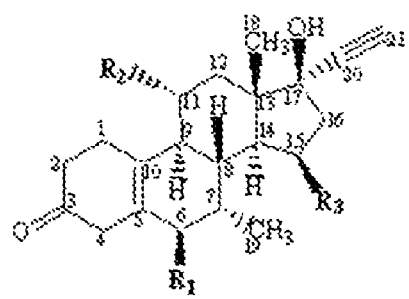
1. $R_1 = R_2 = R_3 = H$
4. $R_1 = OH, R_2 = R_3 = H$
5. $R_1 = R_2 = H, R_3 = OH$
9. $R_1 = H, R_2 = R_3 = OH$
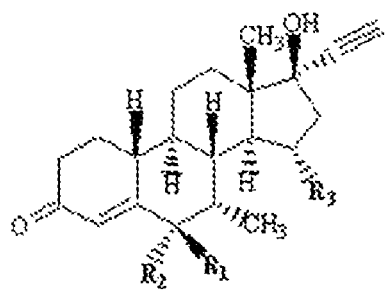
6. $R_1 = R_2 = R_3 = H$
12. $R_1 = OH, R_2 = R_3 = H$
13. $R_1 = R_3 = H, R_2 = OH$
14. $R_1 = R_2 = H, R_3 = OH$
16. $R_1 = OCH_3, R_2 = H, R_3 = H$
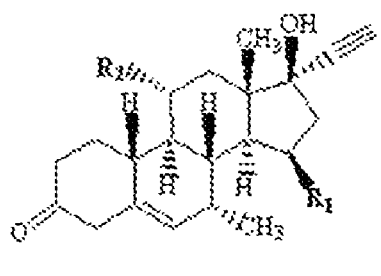
10. $R_1 = R_2 = H$
11. $R_1 = R_2 = OH$
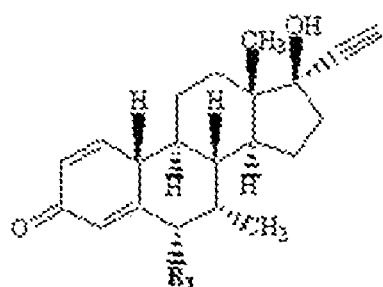
7. $R_1 = H$
15. $R_1 = OH$
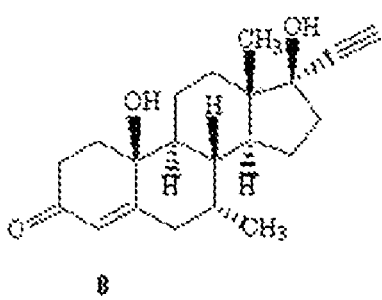
8
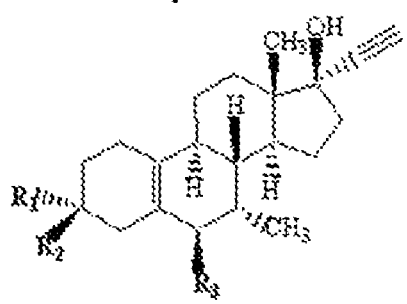
2. $R_1 = R_3 = H, R_2 = OH$
3. $R_1 = OH, R_2 = R_3 = H$
17. $R_1 = H, R_2 = R_3 = OH$
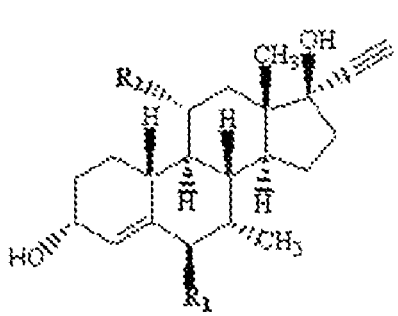
19. $R_1 = OH, R_2 = H$
20. $R_1 = H, R_2 = OH$
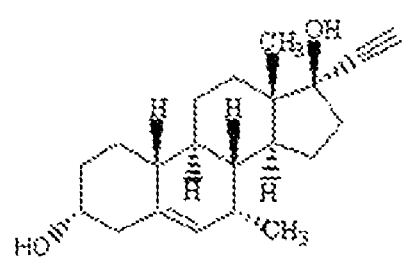
18

METHOD OF PRODUCING TIBOLONE METABOLITES BY FERMENTATION WITH *RHIZOPUS STOLONIFER*

The application is a divisional of U.S. application Ser. No. 11/944,475 filed Nov. 23, 2007, now abandoned.

SUMMARY OF INVENTION

Microbial transformation is an effective tool to synthesize steroidal drugs with potential clinical applications. Such studies are primarily useful in the generation of hydroxylated metabolites for drug toxicity studies. Fungi, bacteria and yeast have been utilized successfully as in vitro models to mimic and predict the metabolic fate of drugs and other xenobiotics in mammalian systems. Previously, many biotransformational studies on various 17α-ethynyl steroids had been carried out with fungal and bacterial strains, which produce hydroxylation of at various positions in the chemical structure.

Tibolone (Compound 1) is a synthetic steroid that combines estrogenic and progestogenic properties with androgenic property, which mimic the action of a male sex hormone. The in vivo metabolism of tibolone (1) in human had been studied with the reference to its three metabolites, 3α-hydroxytibolone, 3β-hydroxytibolone and $\Delta^4$-tibolone.

In the current study, tibolone (1) was used as a structural probe to identify its metabolites produced by a microbial model, and to further investigate the differences between microbial transformation and human metabolism. These metabolic studies showed novel hydroxylation at various positions (Compounds 4-20), in which only Compound 4 was reported previously as metabolite in human metabolism. Compound 1 when incubated with *Rhizopus stolonifer, Fusarium lini, Cunninghamella elegans* and *Gibberella fujikuroi*, resulted in the formation of a library of hydroxyl derivatives. These hydroxytibolones have potential for inhibition of α-glucosidase enzyme.

α-Glucosidase (EC 3.2.1.20) is a typical exo-type glycosidase that releases α-glucosides from the nonreducing end side of the substrates. Diabetes mellitus is a chronic metabolic disorder characterized by high blood glucose levels. Tibolone (1) is used effectively for the treatment of menopausal symptoms and in the prevention of osteoporosis, as a hormone replacement therapy (HRT). The hormone replacement therapy (HRT) effects on glucose metabolism in non-diabetic obese postmenopausal women.

Glucosidase enzymes are involved in several biological processes such as the intestinal digestion, the biosynthesis of glycoproteins and the lysosomal catabolism of the glycoconjugates (Homonojirimycin isomers and N-alkylated homonojirimycins: structural and conformational basis of inhibition of glycosidases. Asano N, Nishida M, Kato A, Kizu H, Matsui K, Shimada Y, Itoh T, Baba M, Watson A A, Nash R J, Lilley P M, Watkin D J, Fleet G W., J Med. Chem. 1998 Jul. 2; 41(14):2565-71). Intestinal α-glucosidases are involved in the final step of the carbohydrate digestion to convert these into monosaccharides which are absorbed from the intestine.

As a result of the catalysis produced by α-glucosidase enzyme in the final step in the digestive process of carbohydrates, its inhibitors can retard the uptake of dietary carbohydrates and suppress postprandial hyperglycemia, and could be useful to treat diabetic and/or obese patients [Novel α-glucosidase Inhibitors with a tetrachlorophthalimide Skeleton., S. Sou, S. Mayumi, H. Takahashi, R. Yamasak, S. Kadoya, M. Sodeoka, and Y. Hashimoto, *Bioorg. Med. Chem. Lett.,* 2000, 10, 1081].

The α-glucosidase inhibitors are effective in lowering the insulin release, insulin requirement and some can lower plasma lipids. The acarbose is a very widely prescribed drug in the management of the type II diabetes and recently a U.S. Pat. No. 6,387,361 to Rosner describes the use of acarbose in the treatment of obesity. According to the criteria issued by WHO (World Health Organization) based on a glucose tolerance test, diabetes mellitus and impaired glucose tolerance (hereinafter sometimes referred to as IGT) are distinguished by the fasting blood glucose level and the blood glucose level 2 hours after glucose loading. Patients with IGT have high blood glucose levels compared to those of patients with diabetes mellitus, and are reported to be at increased risk of developing diabetes mellitus and complications of arteriosclerotic diseases. In particular, it is known that patients with IGT who have blood glucose levels of 170 mg/dl or above at 2 hours following glucose loading, i.e., patients with high-risk IGT, may develop diabetes mellitus at a high rate [Diabetes Frontier, p. 136, 1992]. With regard to voglibose which is an α-glucosidase inhibitor, there are reports of studies on effects of voglibose for insulin-resistant IGT and diabetes [Yakuri-to-Chiryo (Japanese Pharmacology & Therapeutics), 24 (5):213 (1996); Metabol. Exp. Clin., 45:731, 1996]. Voglibose (AO-128) is also known to have effects of lowering blood glucose level and improving glucose tolerance in rats [Yakuri-to-Chiryo (Japanese Pharmacology & Therapeutics), 19 (11):161 (1991); Journal of Nutrition Science and Vitaminology, 45 (1): 33 (1992)]. On the contrary, it has also been reported that the effect of voglibose in improving glucose tolerance could not be verified in human [Rinsho-Seijinbyo, 22 (4): 109 (1992)]. An antibiotic pradimicin Q as α-glucosidase inhibitor is described in the U.S. Pat. No. 5,091,418 to Swada.

In addition, they have also been used as antiobesity drugs, fungistatic compounds, insect anti-feedant, anti-viral and immune modulators [Glycosidase inhibitors and their chemotherapeutic value, Part 1. el Ashry E S, Rashed N, Shobier A H., Pharmazie. 2000 April; 55(4):251-620]. The antiviral activity due to inhibition of α-glucosidase results form abnormal functionality of glycoproteins because of incomplete modification of glycans. Suppression of this process is the basis of antiviral activity [A glucosidase-Inhibitors as potential broad based antiviral agents, Anand Mehta, Nicole Zitzmann, Pauline M. Rudd, Timothy M. Block, Raymond A. Dwek, Febs Letters 430 (1998)17-22] and decrease in growth rate of tumors [Inhibition of experimental metastasis by an alpha-glucosidase inhibitor, 1,6-epi-cyclophellitol. Atsumi S, Nosaka C, Ochi Y, Iinuma H, Umezawa K. Cancer Res. 1993 Oct. 15; 53(20):4896-9]. The α-glucosidase inhibitor N-(1, 3-dihydroxy-2-propyl)valiolamine is described as a promoter of calcium absorption in the U.S. Pat. No. 5,036,081.

In the present invention is reported a surprising discovery that was made when it was discovered that several metabolites of tibolone (1) or its hyroxyderivates obtained by fermentation with various fungi are potent inhibitors of alpha-glucosidase enzyme, a property of these chemicals that has never been reported before in the prior art. Table 1 lists are metabolites of tibolone and their activity against alpha glucosidase enzyme.

TABLE 1

Novel metabolites of tibolone and their activity against alpha-glucosidase enzyme

| Compound | Name | Novel | Active |
|---|---|---|---|
| Compound 1 | Tibolone ($C_{21}H_{28}O_2$) | No | No |
| Compound 2 | 3β-hydroxytibolone ($C_{21}H_{30}O_2$) | No | No |
| Compound 3 | 3α-hydroxytibolone ($C_{21}H_{30}O_2$) | No | No |
| Compound 4 | $\Delta^4$-Tibolone ($C_{21}H_{28}O_2$) | No | Yes |
| Compound 5 | 6β-Hydroxytibolone ($C_{21}H_{28}O_3$) | Yes | Yes |
| Compound 6 | 15β-Hydroxytibolone ($C_{21}H_{28}O_3$) | Yes | No |
| Compound 7 | $\Delta^{1,4}$-Tibolone ($C_{21}H_{26}O_2$) | Yes | Yes |
| Compound 8 | 10β-Hydroxy-$\Delta^4$-tibolone ($C_{21}H_{28}O_3$) | Yes | No |
| Compound 9 | 11α,15β-Dihydroxytibolone ($C_{21}H_{28}O_4$) | Yes | No |
| Compound 10 | 11α,15β-Dihydroxy-$\Delta^5$-tibolone ($C_{21}H_{28}O_4$) | Yes | No |
| Compound 11 | $\Delta^5$-Tibolone ($C_{21}H_{28}O_2$) | Yes | No |
| Compound 12 | 6β-Hydroxy-$\Delta^4$-tibolone ($C_{21}H_{28}O_3$) | Yes | Yes |
| Compound 13 | 6α-Hydroxy-$\Delta^4$-tibolone ($C_{21}H_{28}O_3$) | Yes | Yes |
| Compound 14 | 15α-Hydroxy-$\Delta^4$-tibolone ($C_{21}H_{28}O_3$) | Yes | Yes |
| Compound 15 | 6α-Hydroxy-$\Delta^{1,4}$-tibolone ($C_{21}H_{28}O_3$) | Yes | Yes |
| Compound 16 | 6β-Methoxy-$\Delta^4$-tibolone ($C_{22}H_{30}O_3$) | Yes | No |
| Compound 17 | 3β,6β-Dihydroxytibolone ($C_{21}H_{32}O_3$) | Yes | Not studied |
| Compound 18 | 3α-Hydroxy-$\Delta^5$-tibolone ($C_{21}H_{32}O_2$) | Yes | Not studied |
| Compound 19 | 3α,6β-Dihydroxy-$\Delta^4$-tibolone ($C_{21}H_{32}O_3$) | Yes | Not studied |
| Compound 20 | 3α,11α-Dihydroxy-$\Delta^4$-tibolone ($C_{21}H_{32}O_3$) | Yes | Not studied |

Here we are reporting a new class of α-glucosidase inhibitors i.e., 17α-ethynyl steroids along with comparison of the results with the standard inhibitors of this enzyme and their method of manufacture using microbial fermentation.

DETAILS OF INVENTION

Brief Description of Drawings

FIG. 1 shows the stereochemical structure of the 20 compounds reported in this invention.

FIG. 1

Fermentation of tibolone (1) with *Rhizopus stolonifer* (ATCC 12938) yielded two new mono-hydroxylated metabolites, Compounds 4 and 5, and a known metabolite, Compound 6.

The HREIMS of Compound 4 exhibited the molecular ion ($M^+$) at m/z 328.2171, corresponding to the formula $C_{21}H_{28}O_3$, which indicated that a new oxygen functionality was introduced into the molecule during fermentation period. The IR absorptions were attributed to hydroxyl (3381 $cm^{-1}$) and carbonyl (1705 $cm^{-1}$) functionalities, respectively. The $^1H$ NMR spectrum, compared with that of the substrate, showed a new signal of OH-bearing methine proton at δ 4.04, resonating as a doublet (J=4.0 Hz) with its corresponding carbon resonating at δ 65.9 in $^{13}C$ NMR spectrum which was assigned to C-6 on the basis of HMBC correlations of H-6 (δ 4.04) with C-5 (δ 122.5) and C-10 (δ 128.4). In the $^1H$-$^1H$ COSY 45° spectrum, the aforementioned methine proton showed correlation with the C-7 methine proton resonated at $δ_H$ 2.0. The stereochemistry of C-6 hydroxyl group was determined to be axial by the NOESY correlations between H-6 (δ 4.04) and H-19 (δ 0.76). The above spectral data concluded that Compound 4 has an —OH group at C-6 position as compared to compound 1 and was deduced to be a new metabolite.

The HREIMS of Compound 5 showed the $M^+$ at m/z 328.2070, indicating an increment of 16 mass units as compared to compound 1 in accordance to formula $C_{21}H_{28}O_3$. The $^1H$ and $^{13}C$ NMR data of 5 revealed the presence of a new OH-bearing methine group that resonated at $δ_H$ 4.06 (m, $W_{1/2}$~10.8 Hz) and $δ_C$ 65.5 and deduced for C-15 on the basis of HMBC spectrum correlations, which showed correlation of C-16 protons ($δ_H$ 2.24, 1.7) and C-14 methine proton ($δ_H$ 1.85) with C-15 ($δ_C$ 65.5). The stereochemistry of the newly introduced C-15 hydroxyl group was deduced as β on the basis of NOESY correlations between H-15 ($δ_H$ 4.06) and H-14 ($δ_H$ 1.85) and multiplicity of H-15 signal at δ 4.06 ($W_{1/2}$~10.8 Hz). From these spectral data, the new compound 5 was deduced to 7α-methyl-17α-ethynl-15β,17β-dihydroxy-19-norandrost-5(10)-en-3-one.

The incubation of compound 1 with *Fusarium lini* (ATCC 9593) for 6 days also led to the isolation of a UV active Compound 6 exhibiting the $M^+$ at m/z 312.2023 in HREIMS spectrum ($C_{21}H_{28}O_2$). The $^1H$ NMR spectrum showed a singlet for an olefinic proton at δ 5.82. Its broad-band decoupled $^{13}C$ NMR spectrum showed, in comparison with that of the substrate 1, the disappearance of one quaternary carbon signal resonating at δ 128.2 for C-10 and appearance of an olefinic methine carbon at δ 126.4 which was assigned to the C-4 on the basis of HMQC spectrum, indicating the migration of the C-5/C-10 double bond to C-4/C-5. Thus creating an α,β-unsaturation in Compound 6. The axial orientation of C-10 proton was assigned on the basis of NOESY coupling between H-10 (δ 2.31) and H-8 (δ 1.64). The above spectral data supported the structure of a known Compound 6 as 7α-methyl-17α-ethynl-17β-hydroxy-19-norandrost-4-en-3-one previously isolated during human metabolism of tibolone.

The incubation of 1 (600 mg) with *Cunninghamella elegans* (ATCC 10028b) for six days yielded Compounds 7-10 (FIG. 1). The HREIMS of compound 7 showed the $M^+$ at m/z 310.2004, in accordance with the formula $C_{21}H_{26}O_2$. Comparison between the $^1H$ and $^{13}C$ NMR data of compounds 6 and 7, Compound 7 showed the presence of two additional olefinic signals at δ 7.12 (dd, J=8.4, 4.7 Hz, H-1) and 6.62 (dd, J=8.4, 2.6 Hz, H-2) in the $^1H$ NMR spectrum with the corresponding carbons resonated at δ 153.4 (C-1)

and 127.0 (C-2), respectively, in the $^{13}$C NMR spectrum in compound 7. The presence of a double bond between C-1 and C-2 was further deduced from $^1$H-$^1$H COSY 45° correlations between H-1 (δ 7.12), H-2 (δ 6.62) and H-10 (δ 2.42). While HMBC experiment showed interactions of H-1 with C-2 (δ 127.0) and C-10 (δ 43.0). The final structure of Compound 7 was deduced to be 7α-methyl-17α-ethynl-17β-hydroxy-19-norandrost-1,4-dien-3-one.

The HREIMS of Compound 8 showed the M$^+$ at m/z 328.2090, in agreement with the formula $C_{21}H_{28}O_3$ indicating an introduction of a new oxygen in the molecule, probably in the form of a hydroxyl group. However the $^1$H NMR spectrum displayed no resonance for OH-bearing methine proton, but $^{13}$C NMR spectrum showed a downfield oxygen-bearing quaternary carbon resonated at δ 70.3, which was assigned to C-10 through its HMBC interactions with H-1 (δ 2.36, 2.29) and H-4 (δ 5.77). The 10β-hydroxylation was deduced by the β-SCS (substituents chemical shift) of −5.1, −5.4 and −6.9 ppm for C-2, C-8 and C-11, respectively, and by the downfield shifts of C-1 and C-9 (+5.1 and +7.5, respectively) with respect to the $^{13}$C NMR chemical shifts in compounds 4 and 8. The spectral data supported the structure of a new Compound 8 as 7α-methyl-17α-ethynl-10β,17β-dihydroxy-19-norandrost-4-en-3-one.

The HREIMS of Compound 9 showed the M$^+$ at m/z 344.2212 supporting the formula $C_{21}H_{28}O_4$, indicated that two oxygen had been incorporated into the molecule. The $^1$H and $^{13}$C NMR displayed two OH-bearing methine groups resonating at $\delta_H$ 3.43 (ddd, J=15.1, 11.1, 5.0 Hz); and 4.10 (m, $W_{1/2}$~8.82 Hz) and $\delta_C$ 66.1 and 65.4, respectively. The $^1$H-$^1$H COSY 45° spectrum showed correlations of H-11 (δ 3.43) with H-9 (δ 1.62) and $H_2$-12 (δ 2.05, 1.51), and of H-15 (δ 4.10) with H-14 (δ 1.80) and $H_2$-16 (δ 2.01, 1.55). Hydroxylations at C-11 and C-15 was further supported by HMBC assignments, which has exhibited correlations of $H_2$-12 (δ 2.05, 1.51) and Me-18 (δ 0.90) with C-11 (δ 66.1), and correlation of H-14 (δ 1.80) with δ 65.4 (C-15). The axial orientation of C-11 proton was deduced on the basis of NOESY correlation of H-11 (δ 3.43) with Me-18 (δ 0.90) and multiplicity of H-11 signal resonating at $\delta_H$ 3.43 (ddd, J=15.1, 11.1, 5.0 Hz),[3] while β-stereochemistry of the newly introduced OH group at C-15 was deduced by the NOESY correlations between H-14 (δ 1.80) and H-15 (δ 4.10) and multiplicity of H-15 signal resonating at δ 4.10 ($W_{1/2}$~8.8 Hz). The n-orientation of C-10 proton was similar to compound 6 (FIG. 3). According to this spectral data, the structure was deduced to be 7α-methyl-17α-ethynl-11α,15β,17β-trihydroxy-19-norandrost-5(10)-en-3-one.

The HREIMS of Compound 10 showed the M$^+$ at m/z 344.2341, support formula $C_{21}H_{28}O_4$, with an increment of 32 a.m.u. The UV spectrum showed a weak absorption at 202 nm, while IR showed absorptions at 3312 (OH), 1722 (C=O) and 1652 (C=C) cm$^{-1}$. The $^1$H NMR spectrum showed an upfield doublet of olefinic methine proton at δ 5.42 (J=4.2 Hz, H-6), which showed COSY 45° correlations with H-7 (δ 1.83). Two additional OH-bearing methine protons resonating at δ 3.40 (ddd, J=15.3, 11.0, 4.57 Hz) and 3.91 (m, $W_{1/2}$~9.9 Hz) were unambiguously assigned to H-11 and H-15 through 2D NMR and $^{13}$C NMR spectra. The stereochemistry of newly introduced hydroxyl group at C-11 was deduced to be a (equatorial) on the basis NOESY correlation between H-11 (δ 3.40) and H-18 (δ 0.94) and larger coupling constants (J=15.3 Hz) of H-11 signal. The β-orientation of the OH group at C-15 was deduced on the basis of NOESY correlation between H-14 (δ 1.85) and H-15 (δ 3.91) and multiplicity of H-15 signal, resonating at δ 3.91 (m, $W_{1/2}$~9.9 Hz). The axial β-orientation of C-10 proton was deduced through NOESY cross peaks between H-10 (δ 2.46) and H-8 (δ 1.59). Based on the above mentioned spectral data, the structure was deduced as 7α-methyl-17α-ethynl-11α,15β,17β-trihydroxy-19-norandrost-5-en-3-one.

Tibolone (1) was fermented with *Gibberella fujikuroi* (ATCC 10704) for 12 days yielding six new mono-hydroxylated Compounds 11-16. The HREIMS of Compound 11 showed the M$^+$ at m/z 312.1456 with corresponding formula $C_{21}H_{28}O_2$. The $^1$H NMR spectrum showed an upfield doublet of olefinic proton at δ 5.33 (J=4.7 Hz) which was assigned to H-6 through its $^1$H-$^1$H COSY 45° correlation with H-7 (δ 1.85). The $^{13}$C NMR spectrum showed low-field methine carbon resonated at δ 123.4. A double bond between C-5 and C-6 was deduced through HMBC coupling between H-6 (δ 5.33) and C-7 (δ 34.6). According to the spectral data, the structure was deduced as 7α-methyl-17α-ethynl-17β-hydroxy-19-norandrost-5-en-3-one.

Compounds 12 and 13 were found to be epimers and differentiated on the basis of $^1$H NMR and NOESY experiments. The $^1$H NMR spectrum of Compound 12 displayed a doublet at δ 4.05 (J=4.0 Hz), while compound 13 exhibited a doublet at δ 3.60 (J=6.4 Hz), while $^{13}$C NMR spectra of both the isomers 12 and 13 showed OH-bearing methine carbons resonating at δ 65.9 and 70.0, respectively. The position of the newly introduced hydroxyl at C-6 in both isomers was inferred from the HMBC coupling. The relative configuration in compound 12 of the new hydroxyl group at C-6 was inferred on the basis of coupling pattern and NOESY correlations between H-6 (δ 4.05) and C-19 methyl protons (δ 0.75), while NOESY spectrum of compound 13 also displayed correlations between H-6 (δ 3.60) and C-7 methine proton (δ 1.98). The above spectral data concluded that Compounds 12 and 13 have an —OH group at C-6 position with different orientations.

The molecular formula of Compound 14 was established as $C_{21}H_{28}O_3$ by HREIMS (m/z 328.2132). The $^1$H and $^{13}$C NMR spectra of compound 14 exhibited a OH-bearing methine group resonated at $\delta_H$ 4.02 (m, $W_{1/2}$~14.9 Hz); $\delta_C$ 65.9 and was unambiguously assigned to C-15 on the basis of two-dimensional NMR experiments. In the $^1$H-$^1$H COSY 45° spectrum, the aforementioned methine proton showed correlation with the C-14 methine proton resonating at $\delta_H$ 1.72. This was further supported by the HMBC spectrum, which exhibited correlations of C-14 proton ($\delta_H$ 1.72) with C-15 ($\delta_C$ 65.9). The α-relative configuration of OH group at C-15 was deduced on the basis of multiplicity of H-15 signal resonating at $\delta_H$ 4.02 (m, $W_{1/2}$~14.9 Hz).[12] This spectral data led to the structure 14 as 7α-methyl-17α-ethynl-15β,17β-dihydroxy-19-norandrost-4-en-3-one.

The HREIMS of Compound 15 showed the M$^+$ at m/z 326.2231 ($C_{21}H_{28}O_3$). Two additional doublets in the $^1$H NMR spectrum for two olefinic protons appeared at δ 7.08 (dd, J=8.18, 4.2 Hz) and 6.76 (d, J=8.22 Hz) and one new hydroxymethine proton, appeared at δ 3.81 (d, J=6.4 Hz). The DEPT spectrum of compound 15 showed two olefinic methine carbon signals at δ 154.2 and 126.5, corresponding to a double bond between C-1/C-2, as deduced on the basis of HMBC correlations of H-1 (δ 7.08) with C-2 (δ 126.5) and, of H-2 (δ 6.76) with C-1 (δ 154.2) and C-4 (δ 125.7). One OH-bearing methine carbon resonated at δ 69.8 was assigned to C-6 based on $^3$J correlations between H-6 (δ 3.81) and C-4 (δ 125.7). The α-orientation of newly hydroxyl group at C-6 was deduced to be equatorial on the basis of NOESY correlations between H-6 (δ 3.81) and H-7 (δ 1.95). According to these spectral studies, the structure of Compound 15 was deduced to be 7α-methyl-17α-ethynl-6α,17β-dihydroxy-19-norandrost-1,4-dien-3-one.

The HREIMS of Compound 16 showed the M+ at m/z 343.2356 corresponding to the formula $C_{22}H_{30}O_3$. The $^1$H NMR spectrum of Compound 16 showed the presence of a methoxy singlet resonating at δ 3.47, while geminal methoxy protons were resonated at δ 3.93 (d, J=3.9 Hz). The $^{13}$C NMR spectrum showed a methoxy carbon signal at δ 57.6 and a methoxy-bearing carbon resonated at δ 70.2. The position of the newly introduced methoxy group at C-6 was deduced through HMBC interactions of H-6 (δ 3.93) with C-4 (δ 126.7). The β-orientation of the newly introduced OCH₃ group at C-6 was deduced on the basis of NOESY correlations between H-6 (δ 3.93) and C-19 methyl protons (δ 0.77). The above mentioned spectral data led to conclude that Compound 16 has the structure as 7α-methyl-17α-ethynl-6β-methoxy-17β-hydroxy-19-norandrost-4-en-3-one.

Tibolone (1) (1 g) when reduced with NaBH₄ in dichloromethane yielded reduced products i.e. 3β-hydroxytibolone (2) and 3α-hydroxytibolone (3) in order to check the effect on hydroxylation at various positions in presence of C-3 hydroxyl group (α and β isomers) was investigated. The presence of hydroxyl group at C-3 pronounced the hydroxylation at C-6 as in case of Compounds 17 and 19 and produced better yield of these metabolites as compared to tibolone (1) hydroxyl metabolites. The $^1$H NMR spectra of both the isomers 2 and 3 showed OH-bearing geminal methine protons appeared at δ 3.8 (m, $W_{1/2}$~21.5 Hz) and 4.04 (m, $W_{1/2}$~10.7 Hz), which indicated the reduction of the C-3 ketonic group. The orientation of C-3 methine proton in the both isomers 2 and 3 was deduced from the multiplicity of C-3 proton signals resonated at δ 3.8 (m, $W_{1/2}$~21.5 Hz, H-3a) and 4.04 (m, $W_{1/2}$~10.7 Hz, H-3β), respectively.

Incubation of 3β-hydroxytibolone (2) (300 mg) with *Cunninghamella elegans* for twelve days yielded one hydroxyl-bearing Compound 17. Compound 17 showed the M+ at m/z 330.2346 corresponding to the formula $C_{21}H_{30}O_3$ by HREIMS. The $^1$H NMR spectrum showed a resonance for OH-beared methine proton at δ 3.50 (d, J=3.5 Hz), while corresponding carbon resonated at δ 74.2 in $^{13}$C NMR spectrum. The position of the newly introduced hydroxyl group at C-6 was deduced through HMBC interactions. The α (equatorial) orientation of C-6 proton, geminal to the hydroxyl group, was deduced on the basis of NOESY correlations between H-6 (δ 3.50) and C-19 methyl protons (δ 0.73). The structure of Compound 17 was identified as 7α-methyl-17α-ethynl-3β, 6β,17β-trihydroxy-19-norandrost-5(10)-en-3-one.

Fermentation of 3α-hydroxytibolone (3) (400 mg) with *Cunninghamella elegans* for twelve days yielded three polar Compounds 18-20. Compound 18 showed the M+ at m/z 314.2541 corresponding to the formula $C_{21}H_{30}O_2$ by HREIMS, while the $^1$H and $^{13}$C NMR spectra showed appearance of olefinic proton at 5.38 (d, J=4.5 Hz) with corresponding carbon resonated at δ 132.0 as compared to substrate 3 and was assigned to C-6 methine carbon. The β (axial) orientation of C-10 proton was deduced on the basis of NOESY correlations. From these data, the new compound 18 was identified as 7α-methyl-17α-ethynl-3α,17β-dihydroxy-19-norandrost-5-en-3-one.

The HREI-MS of Compound 19 showed the M+ at m/z 330.2356 corresponding to the formula $C_{21}H_{30}O_3$ by HREIMS. The $^1$H NMR spectrum of 19 showed one additional OH-bearing methine proton signal at δ 4.13 (br. s), while $^{13}$C NMR spectrum showed the resonance of corresponding methine carbon at δ 74.0 (C-6). The $^1$H-$^1$H COSY 45° spectrum also showed an allylic coupling between H-4 and H-6 (δ 4.13). The α (equatorial) orientation of C-6 proton, geminal to hydroxyl group, was deduced on the basis NOESY correlations between H-6 and Me-19 protons (δ 0.87). The structure of Compound 19 was identified as 7α-methyl-17α-ethynl-3α,6β,17β-trihydroxy-19-norandrost-4-en-3-one.

Compound 20 showed the M+ at m/z 330.2256 in HREIMS spectrum in agreement with the formula $C_{21}H_{30}O_3$. The $^1$H and $^{13}$C NMR spectrum of 20 showed an OH-bearing methine group appeared at $δ_H$ 3.80 (ddd, J=13.5, 9.5, 3.3 Hz) and $δ_C$ 66.3 and was established for C-11 through homonuclear COSY correlations between H-11 (δ 3.80), H-18 (δ 1.04) and H₂-12 (δ 2.1, 1.64), while HMBC cross-peak correlations revealed the connectivities between H-11, H-18 (δ 1.04) and C-11 (δ 66.3). The β (axial) orientation of C-11 proton, was geminal to hydroxyl group, was deduced on the basis of larger magnitude of coupling constant of H-11 signal at $δ_H$ 3.82 (ddd, J=13.5, 9.5, 3.3 Hz) and NOESY correlations between H-11 and Me-19 protons (δ 0.88). The structure of Compound 20 was proposed as 7α-methyl-17α-ethynl-3α,11α,17β-trihydroxy-19-norandrost-4-en-3-one.

Some hydroxy metabolites of tibolone (1) showed significant inhibitory activity against enzyme tyrosinas, mainly hydroxylation at C-6, C-11 and C-15 in Compounds 4, 9 and 10 showed pronounced inhibitory activity against enzyme tyrosinas, while α, β unsaturated system (C-4/C-5) in Compound 6 also showed good activity. These metabolites also showed significant inhibitory activity against enzyme α-Glucosidase enzyme. The hydroxyl group at C-6 position (β isomer in Compound 4) showed potent α-Glucosidase inhibitory activity, while other metabolites containing α, β unsaturated system (C-4/C-5) as in Compound 6 and α, β unsaturated system bearing hydroxyl group at C-6 (α and β isomers), C-10β and C-15β showed pronounced inhibitory activities against enzyme α-Glucosidase enzyme as in Compounds 8, 12 and 13. Other α, β unsaturated systems (C-1/C-2, C-4/C-5) in Compound 7 and hydroxyl bearing moiety in Compound 15 also showed significant activity against enzyme α-Glucosidase enzyme. It was concluded that hydroxylation at C-6 position and α, β unsaturated system pronounced inhibitory activity against α-Glucosidase enzyme.

The fermentation of tibolone (1) by fungus yielded thirteen Compounds 4-16. While incubation of hydroxytibolones (2 and 3) with *Cunninghamella elegans* yielded four polar Compounds 17-20. The main hydroxylations occurred in rings B and D, especially at C-6 and C-15(β) positions. The Compounds 4, 5, 9, 10, 12, 13, 14, 15, and 16 were identified as the main metabolites obtained in these fermentations. Compounds 4, 12, 13, and 15 containing an OH-group at C-6 showed pronounced inhibitory activity against α-glucosidase enzyme (Table 2).

TABLE 2

α-Glucosidase inhibitory activities of tibolone (1) and its analogs 4-16, as compared with the reference inhibitors

| Compound | $IC_{50}$ ± S.E.M.[a] (in μM) |
|---|---|
| 1 | NA[b] |
| 4 | 225.0 ± 0.00 |
| 5 | NA[b] |
| 6 | 343.0 ± 0.00 |
| 7 | 227.0 ± 0.02 |
| 8 | 877.0 ± 0.03 |
| 9 | NA[b] |
| 10 | NA[b] |
| 11 | NA[b] |
| 12 | 653.0 ± 0.02 |
| 13 | <70.0 |
| 14 | <70.0 |
| 15 | 340.0 ± 0.02 |
| 16 | NA[b] |

TABLE 2-continued

α-Glucosidase inhibitory activities of tibolone (1) and
its analogs 4-16, as compared with the reference inhibitors

| Compound | $IC_{50} \pm S.E.M.^a$ (in μM) |
|---|---|
| Deoxynojirimycin[c] | 425.6 ± 8.14 |
| Acarbose[c] | 780.0 ± 0.28 |

*Notes:
[a]S.E.M. is the standard error of the mean;
[b]are the inactive compounds and
[c]are the standard inhibitors of the enzyme α-Glucosidase. Compounds 17-20 were not tested due to insufficient quantities.

EXPERIMENTAL DETAILS

General

Melting points were determined on a Yanaco MP-S3 apparatus. UV spectra were measured on a Shimadzu UV 240 spectrophotometer. IR spectra were recorded on a JASCO A-302 spectrophotometer in $CHCl_3$. $^1H$- and $^{13}C$-NMR spectra were recorded on a Bruker Avance AM-400 spectrometer with tetramethylsilane (TMS) as an internal standard. 2D NMR spectra were recorded on a Bruker Avance AMX 500 NMR spectrometer. Optical rotations were measured on JASCO DIP-360 digital polarimeter by using 10 cm cell tube. Mass spectra (EI and HREI-MS) were measured in an electron impact mode on Varian MAT 12 or MAT 312 spectrometers and ions are given in m/z (%). TLC was performed on a pre-coated silica gel card (E. Merck), spots were viewed with ultraviolet light at 254 nm for flouresence quenching spots and at 366 nm for fluorescent spot and stained by spraying with a solution of ceric sulphate in 10% $H_2SO_4$. For column chromatography, silica gel (E. Merck, 230-400 mesh). Tibolone (1) was extracted from Livial-Organon using dichloromethane.

Fungi and Culture Conditions

Microbial cultures of the *Fusarium lini* (ATCC 9593), *Rhizopus stolonifer* (ATCC 12938), *Cunninghamella elegans* (ATCC 10028b) and *Gibberella fujikuroi* were grown on Sabouraud-4% glucose-agar (Merck) at 25° C. and stored at 4° C. *Rhizopus stolonifer* (ATCC 12938) medium was prepared by adding glucose (100 g), peptone (25 g), $KH_2PO_4$ (25 g) and yeast extract (15 g) into distilled water (4 L) and pH was maintained at 5.6. *Fusarium lini* (ATCC 9593) and *Cunninghamella elegans* (ATCC 10028b) media were prepared by mixing the following ingredients into distilled $H_2O$ (3.0 L) in each case: glucose (30.0 g), glycerol (30.0 g), peptone (15.0 g), yeast extract (15.0 g), $KH_2PO_4$ (15.0 g), and NaCl (15.0 g). *Gibberella fujikuroi* medium was prepared by adding the following ingredients into distilled $H_2O$ (3.0 L): glucose (80.0 g), $KH_2PO_4$ (5.0 g), $MgSO_4.2H_2O$ (1.0 g), $NH_4NO_3$ (0.5 g) and *Gibberella* trace element solution (2 mL). The *Gibberella* trace element solution was prepared by mixing $Co(NO_3)_2.6H_2O$ (0.01 g), $FeSO_4.7H_2O$ (0.1 g), $CuSO_4.5H_2O$ (0.1 g), $ZnSO_4.7H_2O$ (0.161 g), $MnSO_4.4H_2O$ (0.01 g) and $NH_4$ molybdate (0.01 g) into distilled water (100 mL).

General Fermentation and Extraction Conditions

The fungal media were transferred into 250 mL conical flasks (100 mL each) and autoclaved at 121° C. Seed flasks were prepared from three-day old slant and fermentation was allowed for two days on a shaker at 25° C. The remaining flasks were inoculated from seed flasks. After two days, tibolone (1) was dissolved in acetone and transferred in each flask (15 mg/0.5 mL) and the flasks were placed on a rotary shaker (128 rpm) at 22° C. for fermentation period. The time course study was carried out after two days and the transformation was analyzed on TLC. The culture media were filtrated and extracted with $CH_2Cl_2$. The extract was dried over anhydrous $Na_2SO_4$, evaporated under reduced pressure and the brown gummy crude was analyzed by thin layer chromatography.

Fermentation of Tibolone (1) with *Rhizopus stolonifer* (ATCC 12938)

Compound 1 (500 mg), dissolved in 15 mL acetone and distributed among 40 flasks and allowed them for fermentation process. All the media were filtered after 3 days and extracted with dichloromethane and evaporated under reduced pressure to finally yield brown thick crude (0.90 mg), and the transformed metabolites were isolated by using column chromatography. Compound 4 (20 mg) was eluted with petroleum ether and EtOAc (60:40), compound 5 (17 mg) with petroleum ether-EtOAc (58:42) and compound 6 (40 mg) with petroleum ether-EtOAc (55:45).

$\Delta^4$-Tibolone (4)

Crystalline solid (20.4 mg); mp 206-208° C.; $[\alpha]^{25}_D$ −145 (c 0.21, $CHCl_3$); UV (MeOH) $\lambda_{max}$ (log ε) 235 (3.2) nm; IR ($CHCl_3$) $v_{max}$ 3402, 2150, 1687, 1667, 1017 $cm^{-1}$; $^1H$ NMR data in $CDCl_3$, Tables 1; $^{13}C$ NMR (100 MHz, $CDCl_3$) δ 198.1 (C-3), 126.4 (C-4), 161.4 (C-5), 38.2 (C-10), 79.1 (C-17), 87.5 (C-20), 74.3 (C-21); EIMS m/z (rel. int. %) 312 ($M^+$, 34,), 245 (53), 229 (33), 187 (17), 173 (18), 161 (20), 147 (28), 135 (56), 121 (23), 109 (32), 107 (43), 105 (39), 95 (24), 91 (62), 81 (34), 79 (59), 67 (58), 55 (100); HREIMS m/z 312.2023 (calculated for $C_{21}H_{28}O_2$, 312.2089).

6β-Hydroxytibolone (5)

White amorphous solid (8.2 mg); mp 186-188° C.; $[\alpha]^{25}_D$ −17 (c 0.35, $CHCl_3$); UV (MeOH) $\lambda_{max}$ (log ε) 204 (3.7) nm; IR ($CHCl_3$) $v_{max}$ 3381, 2150, 1705, 1668, 1043 $cm^{-1}$; $^1H$ and $^{13}C$ NMR data in $CDCl_3$, Tables 1 and 3; EIMS m/z (rel. int. %) 328 ($M^+$, 6), 309 (5), 241 (16), 226 (9), 169 (14), 149 (23), 138 (28), 121 (28), 109 (23), 107 (100), 97 (20), 93 (21), 81 (26), 71 (22), 69 (41), 55 (64); HREIMS m/z 328.2171 (calculated for $C_{21}H_{28}O_3$, 328.2143).

15β-Hydroxytibolone (6)

White solid (7.6 mg); mp 202-205° C.; $[\alpha]^{25}_D$ +16 (c 0.31, $CHCl_3$); UV (MeOH) $\lambda_{max}$ (log ε) 203.4 (3.4) nm; IR ($CHCl_3$) $v_{max}$ 3383, 2162, 1708, 1663, 1050 $cm^{-1}$; $^1H$ and $^{13}C$ NMR data in $CDCl_3$, Tables 1 and 3; EIMS m/z (rel. in %) 328 ($M^+$, 3), 312 (100), 245 (27), 229 (36), 203 (17), 189 (14), 187 (17), 174 (24), 161 (28), 149 (26), 135 (24), 121 (25), 96 (38), 81 (23), 69 (21), 67 (24), 55 (59); HREIMS m/z 328.2070 (calculated for $C_{21}H_{28}O_3$, 328.2038).

Fermentation of Tibolone (1) by *Fusarium lini* (ATCC 9593) and *Cunninghamella elegans* (ATCC 10028b)

Compound 1 (600 mg), dissolved in 18 mL acetone and distributed among 50 flasks, was kept for fermentation. Fermentation was continued for 6 days and then filtrates were extracted with dichloromethane and evaporated under reduced pressure to afford brown thick crude (1.02 gm). Column chromatography technique was used for the separation of Compounds 7-10 from *Cunninghamella elegans* crude while *Fusarium lini* yielded one major Compound 6. Compound 7 (6.2 mg) was eluted with petroleum ether-EtOAc (42:58), compound 8 (15.5 mg) with petroleum ether-EtOAc (38:62), 9 (5.2 mg) with petroleum ether-EtOAc (40:60), whereas compound 10 (10.2 mg) with petroleum ether-EtOAc (30:70).

$\beta^{1,4}$-Tibolone (7)

Amorphous solid (6.2 mg); mp 196-200° C.; $[\alpha]^{25}_D$ −172 (c 0.32, $CHCl_3$); UV (MeOH) $\lambda_{max}$ (log ε) 241.5 (4.1) nm; IR ($CHCl_3$) $v_{max}$ 3303, 2154, 1691, 1666, 1044 $cm^{-1}$; $^1H$ and $^{13}C$ NMR data in CDCl$_3$, Tables 1 and 3; EIMS m/z (rel. int. %) 310 (M$^+$, 42), 241 (100), 230 (11), 199 (17), 187 (27), 161 (22), 149 (34), 145 (17), 119 (18), 109 (14), 91 (62), 67 (62), 55 (100); HREIMS m/z 310.2004 (calculated for C$_{21}$H$_{26}$O$_2$, 310.2011).

10β-Hydroxy-Δ$^4$-tibolone (8)

White powdered solid (15.5 mg); mp 198-201° C.; [α]$^{25}_D$+ 12 (c 0.25, CHCl$_3$); UV (MeOH) λ$_{max}$ (log ε) 239 (2.9) nm; IR (CHCl$_3$) ν$_{max}$ 3345, 2149, 1698, 1649, 1018 cm$^{-1}$; $^1$H and $^{13}$C NMR data in CDCl$_3$, Tables 1 and 3; EIMS m/z (rel. int. %) 328 (M$^+$, 13), 310 (14), 229 (20), 187 (25), 171 (26), 161 (25), 149 (48), 136 (32), 124 (55), 109 (44), 107 (43), 91 (55), 83 (28), 67 (47), 57 (50), 55 (100); HREIMS m/z 328.2090 (calculated for C$_{21}$H$_{28}$O$_3$, 328.2123).

11α,15β-Dihydroxytibolone (9)

White powdered solid (5.2 mg); mp 208-210° C.; [α]$^{25}_D$− 81 (c 0.24, CHCl$_3$); UV (MeOH) λ$_{max}$ (log ε) 203 (3.3) nm; IR (CHCl$_3$) ν$_{max}$ 3342, 2142, 1718, 1636, 1028 cm$^{-1}$; $^1$H and $^{13}$C NMR data in CDCl$_3$, Tables 1 and 3; EIMS m/z (rel. int. %) 344 (M$^+$, 13), 310 (14), 229 (20), 187 (25), 171 (26), 161 (25), 149 (48), 136 (32), 124 (55), 109 (44), 107 (43), 91 (55), 83 (28), 67 (47), 57 (50), 55 (100); HREIMS m/z 344.2212 (calculated for C$_{21}$H$_{28}$O$_4$, 344.2234).

11α,15β-Dihydroxy-Δ$^5$-tibolone (10)

White powdered solid (7.3 mg); mp 207-211° C.; [α]$^{25}_D$+ 27 (c 0.28, CHCl$_3$); UV (MeOH) λ$_{max}$ (log ε) 202.4 (3.4) nm; IR (CHCl$_3$) ν$_{max}$ 3312, 2102, 1722, 1652, 1057 cm$^{-1}$; $^1$H and $^{13}$C NMR data in CDCl$_3$, Tables 1 and 3; EIMS m/z (rel. int. %) 344 (M$^+$, 8), 310 (14), 229 (20), 187 (25), 171 (26), 161 (54), 149 (87), 136 (32), 124 (55), 109 (44), 107 (43), 91 (55), 83 (28), 67 (74), 57 (50), 55 (100); HREIMS m/z 344.2341 (calculated for C$_{21}$H$_{28}$O$_4$, 344.2316).

Fermentation of Tibolone (1) by *Gibberella fujikuroi* (ATCC 10704)

Compound 1 (850 mg) was dissolved in 20 mL acetone and distributed among 30 flasks for fermentation for 12 days. After fermentation, media was extracted with dichloromethane and evaporated to get a crude extract (1.22 gm). Column chromatography technique was used for the separation of Compounds 11-16 from crude extract. Compound 11 (5.2 mg) was eluted with petroleum ether-EtOAc (54:46), compound 12 (10.2 mg) with petroleum ether-EtOAc (50:50), compound 13 (11.2 mg) with petroleum ether-EtOAc (45:55), compound 14 (8.3 mg) with petroleum ether-EtOAc (38:58), compound 15 (9.5 mg) with petroleum ether-EtOAc (30:70) and compound 16 (10.3 mg) with petroleum ether-EtOAc (35:75).

Δ$^5$-Tibolone (11)

White powdered solid (5.6 mg); mp 201-205° C.; [α]$^{25}_D$− 17 (c 0.20, CHCl$_3$); UV (MeOH) λ$_{max}$ (log ε) 203.6 (3.9) nm; IR (CHCl$_3$) ν$_{max}$ 3341, 2157, 1728, 1642, 1088 cm$^{31\ 1}$; $^1$H and $^{13}$C NMR data in CDCl$_3$; EIMS m/z (rel. int. %) 312 (M$^+$, 42), 242 (100), 227 (63), 187 (27), 161 (22), 149 (34), 124 (26), 91 (21), 67 (23), 55 (100); HREIMS m/z 312.1456 (calculated for C$_{21}$H$_{28}$O$_2$, 312.1513).

6β-Hydroxy-Δ$^4$-tibolone (12)

White powdered solid (9.0 mg); mp 189-93° C.; [α]$^{25}_D$− 101 (c 0.41, CHCl$_3$); UV (MeOH) λ$_{max}$ (log ε) 239.5 (2.1) nm; IR (CHCl$_3$) ν$_{max}$ 3332, 2128, 1698, 1651, 1063 cm$^{-1}$; $^1$H and $^{13}$C NMR data in CDCl$_3$, and 3; EIMS m/z (rel. int. %) 328 (M$^+$, 13), 312 (13), 245 (17), 229 (34), 189 (17), 187 (17), 161 (28), 149 (49), 121 (45), 91 (38), 69 (35), 67 (36), 55 (100); HREIMS m/z 328.2176 (calculated for C$_{21}$H$_{28}$O$_3$, 328.2116).

6α-Hydroxy-Δ$^4$-tibolone (13)

White powdered solid (7.0 mg); mp 187-190° C.; [α]$^{25}_D$+ 66.2 (c 0.35, CHCl$_3$); UV (MeOH) λ$_{max}$ (log ε) 240.1 (3.7) nm; IR (CHCl$_3$) ν$_{max}$ 3342, 2106, 1683, 1659, 1061 cm$^{-1}$; $^1$H and $^{13}$C NMR data in CDCl; EIMS m/z (rel. int. %) 328 (M$^+$, 56), 312 (11), 245 (45), 229 (6), 201 (17), 187 (14), 171 (20), 161 (34), 149 (57), 135 (24), 121 (46), 91 (34), 81 (34), 67 (4), 55 (59); HREIMS m/z 328.2132 (calculated for C$_{21}$H$_{28}$O$_3$, 328.2205).

15α-Hydroxy-Δ$^4$-tibolone (14)

White powdered solid (8.3 mg); mp 203-205° C.; [α]$^{25}_D$− 21.3 (c 0.34, CHCl$_3$); UV (MeOH) λ$_{max}$ (log ε) 237.6 (2.6) nm; IR (CHCl$_3$) ν$_{max}$ 3401, 2176, 1691, 1662, 1060 cm$^{-1}$; $^1$H and $^{13}$C NMR data in CDCl$_3$; EIMS m/z (rel. int. %) 328 (M$^+$, 3), 312 (100), 245 (27), 229 (36), 203 (17), 189 (10), 187 (17), 174 (14), 161 (56), 149 (26), 135 (5), 121 (67), 96 (38), 81 (23), 69 (15), 67 (34), 55 (51); HREIMS m/z 328.2212 (calculated for C$_{21}$H$_{28}$O$_3$, 328.2283).

6α-Hydroxy-Δ$^{14}$-tibolone (15)

White powdered solid (5.5 mg); mp 193-196° C.; [α]$^{25}_D$+ 44 (c 0.25, CHCl$_3$); UV (MeOH) λ$_{max}$ (log ε) 244 (3.7) nm; IR (CHCl$_3$) ν$_{max}$ 3441, 2123, 1680, 1637, 1045 cm$^{-1}$; $^1$H and $^{13}$C NMR data in CDCl$_3$; EIMS m/z (rel. int. %) 326 (M$^+$, 13), 312 (34), 245 (27), 229 (67), 203 (5), 189 (14), 187 (14), 174 (24), 161 (56), 149 (26), 135 (24), 121 (100), 96 (45), 81 (23), 69 (12), 67 (24), 55 (34); HREIMS m/z 326.2231 (calculated for C$_{21}$H$_{28}$O$_3$, 326.2292).

6β-Methoxy-Δ$^4$-tibolone (16)

White powdered solid (8.0 mg); mp 206-209° C.; [α]$^{25}_D$− 18 (c 0.42, CHCl$_3$,); UV (MeOH) λ$_{max}$ (log ε) 242.1 (3.1) nm; IR (CHCl$_3$) ν$_{max}$ 3323, 2153, 1691, 1661, 1101 cm$^{-1}$; $^1$H and $^{13}$C NMR data in CDCl$_3$; EIMS m/z (rel. int. %) 343 (M$^+$, 6), 312 (17), 245 (27), 229 (32), 203 (17), 189 (14), 187 (17), 174 (25), 161 (28), 149 (26), 135 (24), 121 (25), 91 (100), 81 (23), 69 (21), 67 (23), 55 (45); HREIMS m/z 343.2356 (calculated for C$_{22}$H$_{30}$O$_3$, 343.2338).

Fermentation of 3β-Hydroxytibolone (2) by *Cunninghamella elegans* (ATCC 10028b)

Compound 1 (1 g) was dissolved in dry dichloromethane (100 mL) and cooled in an ice bath to 0° C. Sodium borohydride (500 mg) was added to the solution in portions whilst stirring. The mixture was stirred at room temperature for five hours. Acetic acid (50 mL) was destroyed the excess Sodium borohydride and the dichloromethane was removed in vacuo. Water (100 mL) was added to the resulting oily product, and the suspension was extracted with ethyl acetate (1 L). The ethyl acetate extract was washed with sodium hydrogen carbonate solution (300 mL), water and brine. The removal of the solvent on a rotary evaporator afforded crude extract (1.2 g). Column chromatography technique was used for the separation of these hydroxytibolones, compounds 2 and 3.

Compound 2 (300 mg) was eluted with petroleum ether-EtOAc (50:50) and compound 3 (400 mg) was eluted with petroleum ether-EtOAc (48:52). Compound 2 (300 mg), dissolved in 15 mL acetone and distributed among 40 flasks, was kept for fermentation. Fermentation was continued for 12 days and then filtrates were extracted with CH$_2$Cl$_2$ and evaporated under reduced pressure to afford brown thick crude (0.81 gm). Column chromatography technique was used for the separation of one hydroxyl Compound 17 from crude extract. Compound 17 (6.2 mg) was eluted with petroleum ether-EtOAc (40:60).

3β,6β-Dihydroxytibolone (17)

White powdered solid (4.2 mg); mp 206-209° C.; [α]$^{25}_D$+ 105 (c 0.31, CHCl$_3$); UV (MeOH) λ$_{max}$ (log ε) 201 (3.1) nm; IR (CHCl$_3$) ν$_{max}$ 3353, 2164, 1663, 1078 cm$^{-1}$; $^1$H and $^{13}$C NMR data in CDCl$_3$; EIMS m/z (rel. int. %) 330 (M$^+$, 7), 312 (17), 245 (27), 229 (32), 203 (17), 189 (14), 187 (17), 174

(25), 161 (28), 149 (26), 135 (24), 121 (25), 91 (100), 81 (23), 69 (21), 67 (23), 55 (45); HREIMS m/z 330.2346 (calculated for $C_{21}H_{32}O_3$, 328.2374).

Fermentation of 3α-Hydroxytibolone (3) by *Cunninghamella elegans* (ATCC 10028b) Compound 3 (400 mg), dissolved in 18 mL acetone and distributed among 50 flasks, was kept for fermentation. Fermentation was continued for 12 days and then filtrates were extracted with dichloromethane and evaporated under reduced pressure to afford brown thick crude (0.89 gm). Column chromatography technique was used for the separation of hydroxy Compounds 18-20 from crude extract. Compound 18 (11.3 mg) was eluted with petroleum ether-EtOAc (40:60). Compound 19 (5.2 mg) was eluted with petroleum ether-EtOAc (54:46) and compound 20 (10.2 mg) with petroleum ether-EtOAc (50:50).

3α-Hydroxy-$\Delta^5$-tibolone (18)

White powdered solid (4.6 mg); mp 206-207° C.; $[\alpha]^{25}_D$+ 52.2 (c 0.23, CHCl$_3$); UV (MeOH) $\lambda_{max}$ (log ε) 204.2 (4.0) nm; IR (CHCl$_3$) $\nu_{max}$ 3313, 2154, 1646, 1038 cm$^{-1}$; $^1H$ and $^{13}C$ NMR data in CDCl$_3$; EIMS m/z (rel. int. %) 314 (M$^+$, 8), 312 (17), 245 (27), 229 (32), 203 (17), 189 (14), 187 (17), 174 (25), 161 (28), 149 (21), 135 (24), 121 (23), 91 (11), 81 (23), 69 (21), 67 (21), 55 (45); HREIMS: m/z 314.2541 (calculated for $C_{21}H_{32}O_2$, 314.2597).

3α,6β-Dihydroxy-$\Delta^4$-tibolone (19)

White powdered solid (4.2 mg); mp 201-205° C.; $[\alpha]^{25}_D$- 18 (c 0.31, CHCl$_3$); UV (MeOH) $\lambda_{max}$ (log ε) 201.2 (2.9) nm; IR (CHCl$_3$) $\nu_{max}$ 3323, 2156, 1665, 1118 cm$^{-1}$; $^1H$ and $^{13}C$ NMR data in CDCl$_3$; EIMS m/z (rel. int. %) 330 (M$^+$, 6), 312 (17), 245 (27), 229 (32), 203 (17), 189 (14), 187 (14), 174 (25), 161 (21), 149 (26), 135 (22), 121 (25), 91 (100), 81 (23), 69 (21), 67 (23), 55 (45); HREIMS m/z 330.2356 (calculated for $C_{21}H_{32}O_3$, 330.2338).

3α,11α-Dihydroxy-$\Delta^4$-tibolone (20)

White powdered solid (5.1 mg); mp 199-201° C.; $[\alpha]^{25}_D$+ 61 (c 0.45, CHCl$_3$); UV (MeOH) $\lambda_{max}$ (log ε) 202.6 (3.5) nm; IR (CHCl$_3$) $\nu_{max}$ 3323, 2143, 1668, 1105 cm$^{-1}$; $^1H$ and $^{13}C$ NMR data in CDCl$_3$; EIMS m/z (rel. int. %) 330 (M$^+$, 4), 312 (14), 245 (27), 229 (42), 203 (17), 189 (34), 187 (17), 174 (19), 161 (28), 149 (26), 135 (35), 121 (25), 91 (98), 81(23), 69 (67), 67 (23), 55 (51); HREIMS m/z 330.2256 (calculated for $C_{21}H_{32}O_3$, 330.2238).

α-Glucosidase Enzyme Inhibition Assay

α-Glucosidase (E.C.3.2.1.20) enzyme inhibition assay has been performed according to the slightly modified method of Matsui et al. α-Glucosidase (E.C.3.2.1.20) from *Saccharomyces* sp. was purchased from Wako Pure Chemical Industries Ltd. (Wako 076-02841). The inhibition has been measured spectrophotometrically at pH 6.9 and at 37° C. using 0.7 mM p-nitrophenyl α-D glucopyranoside (PNP-G) as a substrate and 250 m units/mL enzyme in 50 mM sodium phosphate buffer containing 100 mM NaCl. 1-Deoxynojirimycin (0.425 mM) and acarbose (0.78 Mm) were used as positive controls. The increment in absorption at 400 nm due to the hydrolysis of PNP-G by α-glucosidase was monitored continuously with the spectrophotometer (Molecular Devices, USA). The concentrations of the test compounds, which inhibited the hydrolysis of PNP-G by α-glucosidase by 50% (IC$_{50}$), were determined by monitoring the effect of increasing the concentration of these compounds on the inhibition values. The IC$_{50}$ values were then calculated using EZ-Fit enzyme kinetics program (Perrella Scientific Inc., Amherst, Mass., U.S.A.).

REFERENCES

1. Choudhary, M. I.; Nasir, M.; Khan, S. N.; Atif, M.; Ali, R. A.; Khalil, S. M.; Atta-ur-Rahman *Z. Naturforsch.* 2007, 62b, 593-599.
2. Choudhary, M. I.; Yousuf, S.; Samreen.; Shah, S. A. A.; Ahmed, S.; Atta-ur-Rahman *Chem. Pharma. Bull.* 2006, 54, 927-930.
3. Choudhary, M. I; Shah, S. A. A. Sami, A.; Ajaz, A.; Shaheen, F.; Atta-ur-Rahman *Chem. Biodiv.* 2005, 2, 516-524.
4. Choudhary, M. I.; Batool, I.; Shah, S. A. A.; Nawaz, S. A.; Atta-ur-Rahman *Chem. Pharma. Bull.* 2005, 53, 1455-1459.
5. Choudhary, M. I.; Sultan, S.; Jalil, S.; Anjum, S.; Rahman, A. A.; Fun, H. K.; Atta-ur-Rahman *Chem. Biodiv.* 2005, 2, 392-400.
6. Da-Fang, Z.; Lu, S.; Lei, L.; Hai-Hua, H. *Acta. Pharmacol.* 2003, 24, 442-447.
7. Moody, J. D.; Zhang, D.; Heinze, T. M.; Cerniglia, C. E. *Appl. Envirn. Microbiol.* 2000, 66, 3646-3649.
8. Abourashed, E. A.; Clark, A. M.; Hufford, C. D. *Curr. Med. Chem.* 1999, 6, 359-374.
9. Chatterjee, P.; Kauzi, S. A.; Pezzuto, J. M.; Hamann, M. T. *Appl. Envirn. Microbiol.* 2000, 66, 3850-3855.
10. Kent, U. M.; Jushchyshyn, M. I.; Hollenberg, P. F. *Curr. Drug. Meta.* 2001, 2, 215-243.
11. Hu, S. H.; Tian, X. F.; Sun Y. H.; Han, G. D. *Steroids* 1996, 61, 407-410.
12. Hu, S. H; Tian, X. F.; Han, G. D. *Steroids* 1998, 63, 88-92.
13. Choudhary, M. I.; Musharraf, S. G.; Ali, R. A.; Atif, M.; Atta-ur-Rahman *Z. Naturforsch.* 2004, 59b, 323-328.
14. Ederveen, A. J.; Kloosterboer, H. J. *J. Bone Miner. Res.* 1999, 14, 1963-1970.
15. Kloosterboer, H. J. *J. Steroid Biochem. Mol. Biol.* 2001, 76, 231-238.
16. Vos, R. M. E.; Krebbers, S. F. M.; Verhoever, C. H. J.; Delbressine, L. P. C. *Drug. Metabol. disposi.* 2002, 30, 106-112.
17. Steckelbroeck, S.; Jin Y.; Oyesanmi, B.; Kloosterboer, H. J.; Penning, T. M. *Mol. Pharmacol.* 2004, 66, 1702-1711.
18. Helenius, J.; Kloosterboer, H. J. *Maturitas,* 2004, 48, 30-40.
19. Yazigi, R.; Sahid, S.; Contreras, L.; Rodriguez, T. *Gyneco. Onco.* 2004, 93, 568-570.
20. Morin-Papunen, L. C.; Vauhkonen. I.; Ruokonen, A.; Tapanainen, J. S.; Raudaskoski, T. *Eur. J. Endocrinol.* 2004, 150, 705-714.
21. Choudhary, M. I.; Musharraf, S. G.; Khan, M. T. H.; Abdelrahman, D.; Parvaz, M.; Shaheen, F.; Atta-ur-Rahman *Helv. Chim. Acta.* 2003, 86, 3450-3460.
22. Choudhary, M. I.; Shah, S. A. A.; Musharraf, S. G.; Shaheen, F.; Atta-ur-Rahman *Nat. Prod. Res.* 2003, 17, 215-220.
23. Choudhary, M. I.; Musharraf, S. G.; Shaheen, F.; Atta-ur-Rahman *Nat. Prod. Lett.* 2002, 16, 377-382.
24. Choudhary, M. I.; Azizuddin.; Atta-ur-Rahman *Nat. Prod. Lett.* 2001, 16, 101-106.
25. Atta-ur-Rahman, Choudhary, M. I.; Asif, F.; Farooq, A.; Yaqoob, M. *Nat. Prod. Lett.* 2000, 14, 217-224.
26. Atta-ur-Rahman, Choudhary, M. I.; Asif, F.; Farooq, A.; Yaqoob, M.; Dar, A. *Phytochemistry* 1998, 49, 2341-2342.
27. Atta-ur-Rahman, Yaqoob, M.; Farooq, A.; Anjum, S.; Asif, F.; Choudhary, M. I. *J. Nat. Prod.* 1998. 61, 1340-1342.
28. Atta-ur-Rahman, Choudhary, M. I.; Shaheen, F.; Ashraf, M.; Jahan, S. *J. Nat. Prod.* 1998, 61, 428-431.
29. Atta-ur-Rahman, Farooq, A.; Anjum, S.; Choudhary, M. I. *Curr. Org. Chem.* 1999, 3, 309-312.
30. Atta-ur-Rahman, Farooq, A.; Choudhary, M. I. *J. Nat. Prod.* 1997, 60, 1038-1040.
31. Chiba, S. *Biosci. Biotech. Biochem.* 1997, 61, 1233-1239.

32. Crespo, C. J.; Smit, E.; Snelling A.; Sempos, C. T.; Andersen, R. E. *Diabetes Care* 2002, 25, 1675-1680.
33. Egarter, C.; Huber, J.; Haidbauer, R.; Pusch, H.; Fischl, F.; Putz, M. *Maturitas* 1996, 23, 55-62.
34. Castelo-Branco, C.; Vicente, J. J.; Figueras, F.; Sanjuan, A.; deOsaba, M. J. M.; Casals, E.; Pons, F.; Balasch, J.; Vanrell, J. A. *Maturitas* 2000, 32, 161-168.
35. Kamel, H. K.; Perry, H. M.; Morley, J. E. *J. Am. Geriatr. Soc.* 2001, 49, 179-187.
36. Iqbal, M. M. *South Med. J.* 2000, 93, 2-18.
37. Lindsay, R.; Cosman, F.; Lobo, R. A.; Walsh, B. W.; Harris, S. T.; Reagan, J. E.; Liss, C. L.; Melton, M. E.; Byrnes C. A. *J. Clin. Endocrinol. Metab.* 1999, 84, 3076-3081.
38. Shiino, M.; Watanabe, Y.; Umezawa, K. Bioorg. *Med. Chem.* 2001, 9, 1233-1240.
39. Hanson, J. R.; Nasir, H.; Parvez, A. *Phytochemistry* 1996, 42, 411-415.
40. Lee, P.; Kitamura, Y.; Kaneko, K.; Shiro, M.; Xu, G. J.; Chen, Y. P. *Chem. Pharma. Bull.* 1988, 36, 4316-4329.
41. Hearing, V. J. *Methods Enzymol.* 1987, 142, 154-165.
42. Matsui, T.; Yoshimoto, C.; Osajima, K.; Oki, T.; Osajima, Y. *Biosci. Biotech. Biochem.* 1996, 60, 2010.

What is claimed is:

1. A microbial method of producing 6β-Hydroxytibolone, 15β-Hydroxytibolone, and Δ4-Tibolone by growing *Rhizopus stolonifer* (TSY 0471) in a nutrient media containing tibolone.

* * * * *